(12) United States Patent
Zhu et al.

(10) Patent No.: US 11,413,153 B2
(45) Date of Patent: Aug. 16, 2022

(54) BIONIC ARTIFICIAL HIP JOINT

(71) Applicant: Hongwen Zhu, Tianjin (CN)

(72) Inventors: Hongwen Zhu, Tianjin (CN); Guofu Huang, Tianjin (CN); Ronghua Dong, Tianjin (CN); Tianmou Zhu, Tianjin (CN)

(73) Assignee: Hongwen Zhu, Tianjin (CN)

( * ) Notice: Subject to any disclaimer, the term of this patent is extended or adjusted under 35 U.S.C. 154(b) by 56 days.

(21) Appl. No.: 17/088,400

(22) Filed: Nov. 3, 2020

(65) Prior Publication Data

US 2021/0045882 A1 Feb. 18, 2021

(51) Int. Cl.
*A61F 2/36* (2006.01)
*A61F 2/30* (2006.01)

(52) U.S. Cl.
CPC .... *A61F 2/367* (2013.01); *A61F 2002/30153* (2013.01); *A61F 2002/30428* (2013.01); *A61F 2002/30433* (2013.01); *A61F 2002/30449* (2013.01); *A61F 2002/368* (2013.01)

(58) Field of Classification Search
CPC ................ A61F 2002/368; A61F 2/367; A61F 2002/4066; A61F 2002/4062; A61F 2002/4074; A61F 2/30723; A61F 2/30734; A61F 2002/2825; A61F 2002/2835; A61F 2002/30769; A61F 2002/30911; A61F 2/30907; A61F 2002/30915; A61F 2002/30919; A61F 2002/3092; A61F 2/30749; A61F 2/30742; A61F 2/30739; A61F 2/30744
See application file for complete search history.

(56) References Cited

U.S. PATENT DOCUMENTS

| | | | | |
|---|---|---|---|---|
| 4,064,567 A * | 12/1977 | Burstein | ................ | A61L 27/18 623/23.46 |
| 4,287,617 A * | 9/1981 | Tornier | ................ | A61F 2/3662 623/23.32 |
| 4,718,915 A * | 1/1988 | Epinette | .................... | A61F 2/36 623/23.28 |
| 4,938,771 A * | 7/1990 | Vecsei | .................... | A61F 2/367 623/23.15 |
| 5,015,817 A * | 5/1991 | Kranz | .................. | A61F 2/3662 219/121.64 |
| 5,035,714 A * | 7/1991 | Willert | ................ | A61F 2/30734 623/23.62 |
| 5,108,432 A * | 4/1992 | Gustavson | .......... | A61F 2/30734 623/23.54 |

(Continued)

*Primary Examiner* — Alvin J Stewart

(74) *Attorney, Agent, or Firm* — CBM Patent Consulting, LLC

(57) ABSTRACT

The invention discloses a bionic artificial hip joint. The artificial hip joint includes a femoral stem located above corpus femoris, and a convex force-bearing part is provided on the femoral stem. The force-bearing part abuts against the inner side of the cortex on greater trochanter and bears a part of the longitudinal stress; its hollow design is convenient for bone grafting, so that the prosthesis and the greater trochanter can be integrated. Replacement surgery can preserve the hard cortex on the greater trochanter, providing another focus point for the femoral stem and further improving the stability of the connection between the bionic artificial hip joint and corpus femoris.

6 Claims, 5 Drawing Sheets

(56) References Cited

U.S. PATENT DOCUMENTS

| | | | | |
|---|---|---|---|---|
| 5,133,767 A * | 7/1992 | Frey | A61B 17/8841 | 623/23.54 |
| 5,152,798 A * | 10/1992 | Kranz | A61F 2/3662 | 623/23.33 |
| 5,163,961 A * | 11/1992 | Harwin | A61F 2/30739 | 623/22.46 |
| 5,192,331 A * | 3/1993 | Spotorno | A61F 2/367 | 623/23.28 |
| 5,201,766 A * | 4/1993 | Georgette | A61L 27/06 | 623/923 |
| 5,496,375 A * | 3/1996 | Sisk | A61F 2/367 | 623/23.54 |
| 5,676,700 A * | 10/1997 | Black | A61L 27/3608 | 623/23.28 |
| 6,238,436 B1 * | 5/2001 | Lob | A61F 2/4637 | 623/23.18 |
| 6,334,874 B1 * | 1/2002 | Tornier | A61F 2/4014 | 623/19.14 |
| 6,406,496 B1 * | 6/2002 | Ruter | A61F 2/4059 | 623/19.14 |
| 6,409,768 B1 * | 6/2002 | Tepic | A61B 17/1753 | 623/23.27 |
| 6,436,144 B1 * | 8/2002 | Ahrens | A61F 2/4059 | 623/19.11 |
| 6,440,171 B1 * | 8/2002 | Doubler | A61F 2/36 | 623/22.42 |
| 6,641,616 B1 * | 11/2003 | Grundei | A61F 2/36 | 623/23.26 |
| 6,899,736 B1 * | 5/2005 | Rauscher | A61F 2/40 | 623/19.12 |
| 7,179,259 B1 * | 2/2007 | Gibbs | A61F 2/4603 | 606/98 |
| 8,118,868 B2 * | 2/2012 | May | A61F 2/367 | 623/13.14 |
| 8,182,542 B2 * | 5/2012 | Ferko | A61F 2/3877 | 623/19.13 |
| 8,292,967 B2 * | 10/2012 | Brown | A61F 2/30907 | 623/23.19 |
| 8,308,806 B2 * | 11/2012 | Grant | A61F 2/40 | 623/19.14 |
| 8,585,770 B2 * | 11/2013 | Meridew | A61F 2/30724 | 623/23.46 |
| 8,623,092 B2 * | 1/2014 | Bickley | A61F 2/40 | 623/18.11 |
| 8,979,940 B2 * | 3/2015 | Porter | A61F 2/3609 | 623/23.15 |
| 9,345,576 B2 * | 5/2016 | Shea | A61F 2/30734 | |
| 9,345,580 B2 * | 5/2016 | Porter | A61F 2/0811 | |
| 11,147,679 B2 * | 10/2021 | Kowalczyk | A61F 2/2846 | |
| 2001/0014829 A1 * | 8/2001 | Yoon | A61F 2/30907 | 623/23.46 |
| 2001/0016780 A1 * | 8/2001 | Yong San | A61F 2/30907 | 623/23.46 |
| 2001/0018617 A1 * | 8/2001 | Copf | A61F 2/36 | 623/23.26 |
| 2003/0187513 A1 * | 10/2003 | Durniak | A61B 17/8802 | 623/23.62 |
| 2004/0034431 A1 * | 2/2004 | Maroney | A61B 17/154 | 623/19.14 |
| 2004/0102854 A1 * | 5/2004 | Zhu | A61L 27/16 | 623/23.15 |
| 2004/0117024 A1 * | 6/2004 | Gerbec | A61F 2/38 | 623/20.15 |
| 2004/0122525 A1 * | 6/2004 | Daniels | A61F 2/4684 | 623/22.42 |
| 2004/0199259 A1 * | 10/2004 | Pichon | A61F 2/30734 | 623/23.23 |
| 2004/0267267 A1 * | 12/2004 | Daniels | A61B 17/1617 | 623/22.42 |
| 2005/0004679 A1 * | 1/2005 | Sederholm | A61F 2/36 | 623/22.46 |
| 2005/0043811 A1 * | 2/2005 | Doubler | A61F 2/36 | 623/23.18 |
| 2005/0119759 A1 * | 6/2005 | Tuke | A61F 2/468 | 623/22.41 |
| 2005/0177241 A1 * | 8/2005 | Angibaud | A61F 2/4014 | 623/19.14 |
| 2006/0200249 A1 * | 9/2006 | Beguin | A61F 2/4014 | 623/19.14 |
| 2006/0229734 A1 * | 10/2006 | Yoon | A61L 27/12 | 623/23.46 |
| 2006/0241776 A1 * | 10/2006 | Brown | A61B 17/7225 | 623/22.32 |
| 2007/0129809 A1 * | 6/2007 | Meridew | A61F 2/30728 | 623/22.32 |
| 2008/0147187 A1 * | 6/2008 | Bollinger | A61F 2/367 | 29/445 |
| 2008/0177393 A1 * | 7/2008 | Grant | A61F 2/40 | 623/20.11 |
| 2008/0234829 A1 * | 9/2008 | Mutchler | A61F 2/4014 | 623/19.14 |
| 2009/0270860 A1 * | 10/2009 | Bergin | A61F 2/3662 | 606/62 |
| 2009/0317447 A1 * | 12/2009 | Hsiao | A61F 2/2875 | 623/23.61 |
| 2010/0076572 A1 * | 3/2010 | Jamali | A61F 2/2846 | 606/86 R |
| 2011/0009973 A1 * | 1/2011 | Meyers | A61F 2/389 | 623/18.11 |
| 2011/0029089 A1 * | 2/2011 | Giuliani | A61F 2/40 | 623/19.14 |
| 2011/0130840 A1 * | 6/2011 | Oskouei | A61F 2/4059 | 623/18.11 |
| 2011/0144756 A1 * | 6/2011 | Bickley | A61F 2/40 | 623/18.11 |
| 2011/0218641 A1 * | 9/2011 | Smith | A61F 2/367 | 623/22.42 |
| 2012/0010720 A1 * | 1/2012 | Dickerson | A61F 2/36 | 623/22.42 |
| 2012/0101583 A1 * | 4/2012 | Lascar | A61F 2/4059 | 623/19.14 |
| 2013/0218282 A1 * | 8/2013 | Hunt | A61F 2/30 | 623/23.42 |
| 2014/0172113 A1 * | 6/2014 | Shea | A61F 2/34 | 623/22.21 |
| 2015/0173908 A1 * | 6/2015 | Shimozono | A61F 2/30907 | 623/20.36 |
| 2015/0223940 A1 * | 8/2015 | Papadonikolakis | A61F 2/40 | 623/19.14 |
| 2016/0310281 A1 * | 10/2016 | Yeh | A61F 2/3672 | |
| 2017/0095337 A1 * | 4/2017 | Pasini | A61F 2/36 | |
| 2019/0110897 A1 * | 4/2019 | Sunavala-Dossabhoy | A61F 2/34 | |
| 2019/0224015 A1 * | 7/2019 | Woods | A61F 2/3662 | |
| 2019/0231544 A1 * | 8/2019 | Boileau | A61F 2/4014 | |
| 2020/0129297 A1 * | 4/2020 | Haidukewych | A61F 2/3601 | |
| 2022/0000624 A1 * | 1/2022 | Prevot | A61F 2/3676 | |

* cited by examiner

BIONIC ARTIFICIAL HIP JOINT

This application claims priority to Chinese Patent Application Ser. No. CN2019110719964 filed on 5 Nov. 2019.

TECHNICAL FIELD

The invention relates to a medical artificial joint prosthesis, in particular a bionic artificial hip joint.

BACKGROUND ART

The human hip joint is the joint formed by the thigh bone (femur) and the pelvis. The hip joint is a spherical joint that includes a spherical femoral head and a bowl-shaped acetabulum. The spherical outer surface and the bowl inner surface are both covered with smooth cartilage, and the synovial membrane secretes mucus to minimize friction. When the hip joint develops a disease, the cartilage is no longer smooth, and the synovial sac shrinks due to inflammation, so the hip joint can no longer function as usual. When the hip joint leads to pain, stiffness or deformation due to degeneration, disease, or trauma, or even lead to inconvenient movement, and the symptoms cannot be relieved by drugs or other treatments, replacement of an artificial hip joint will generally be arranged by surgery for the patient, so that the patient can restore his daily activity ability.

The artificial hip joint prosthesis imitates the structure of the human hip joint, including a prosthetic metal cup used to replace the acetabulum and a spherical end used to replace the femoral head, wherein the spherical end is fixed on the femoral stem. The lower end of the femoral stem is provided with a bolt, and the femoral stem is fixed on the human femur by inserting the bolt into the femoral medullary cavity. The spherical end forms a rotating mechanism with the acetabulum or the prosthetic metal cup to realize the bending and movement of the femur.

In the existing artificial hip replacement surgery, it is possible to choose a bowl-shaped acetabulum for replacement, or a femoral stem with a spherical end for replacement according to the specific injury and condition, or both at the same time. But after a period of time, the tightness between the femoral stem and the femur on which it is located gradually decreases, and the two will become loose. Under the action of body pressure, the femoral stem and the bolt on it will sink further, causing the two legs of the patient to have different lengths, which will further affect the normal physiological function of the hip joint.

In view of the above problems, the inventor has conducted in-depth research on the existing bionic artificial hip joints, and found that the bolts on the existing femoral stems are all straight rod-shaped. In order to insert the bolts into the medullary cavity of the femur, the doctor needs to drill a deep hole in the middle of the patient's medullary cavity. For the hole, a vertical hole is naturally preferred. However, the human femur is physiologically curved, not truly straight rod-shaped. Thus, while preparing for holes required for installing existing artificial hip joints, it is necessary to destroy not only the cancellous bone, but also part of the cortex, which reduces the overall strength of the femur. Moreover, the straight rod-shaped structure mainly focuses on the inner condyle regarding bearing capacity of the vertical force.

Moreover, in order to install the existing artificial hip joint, it is necessary to remove the femoral head, femoral neck and part of the cortex on the greater trochanter, which weakens the connection between the corpus femoris and the artificial hip joint.

In addition, the existing artificial hip joint and the corpus femoris are in a hard-to-hard connection, lacking a buffer mechanism. As such, any attempt to walk will result in a rigid impact, which will inevitably lead to more serious wear and tear over the years.

These are the direct reasons leading to the disadvantages of bionic artificial hip joint in the existing technology, such as insufficient durability, insufficient strength, and susceptibility to deformation of the connection with the femur.

Contents of the Invention

In order to overcome the above problems, the present inventors have conducted intensive research and devised a bionic artificial hip joint. The artificial hip joint includes a femoral stem located above corpus femoris, and a convex force-bearing part is provided on the femoral stem. The force-bearing part abuts against the inner side of the cortex on greater trochanter and bears a part of the longitudinal stress. The hollow design of the force-bearing part is convenient for bone grafting, so that the prosthesis and the cortex on greater trochanter can be integrated to improve the stability of the connection between the bionic artificial hip joint and corpus femoris. In the middle and lower part of the femoral stem, there is a design with a predetermined curvature. This design enables the femoral stem to be inserted into the corpus femoris along the physiological curvature of the femoral medullary cavity. Therefore, the artificial hip joint and the corpus femoris are tightly connected as a whole without excessive destruction of the substantia *compacta* in the femoral medullary cavity, which makes the strength of corpus femoris after surgery higher, and can also make the corpus femoris and the femoral stem more tightly fixed, not easy to loosen and break. As such, the present invention is provided.

Specifically, the object of the present invention is to provide a bionic artificial hip joint which includes a femoral stem 1 located above corpus femoris;

a convex force-bearing part 2 is provided on the femoral stem 1;

the femoral stem 1 can be combined with a cortex on greater trochanter via the force-bearing part 2.

The force-bearing part 2 abuts against the inner side of the cortex on greater trochanter.

Wherein the force-bearing part 2 can be integrated with the cortex on greater trochanter.

Wherein the force-bearing part 2 is located on a side of the femoral stem 1, and has an arc-shaped outside.

Wherein a reserved space 21 capable of containing bone cement is provided inside the force-bearing part 2.

Wherein a hole 22 communicating with the reserved space 21 is opened via a surface of the force-bearing part 2.

Preferably, the surface of the force-bearing part 2 is net-shaped.

Wherein the surface of the force-bearing part 2 is a net-shaped hard shell 23.

The hard shell 23 is detachably fixed on the force-bearing part 2.

Wherein, in the force-bearing part 2, a support ridge 24 is provided on the inner side of the hard shell 23 to support the hard shell 23.

Wherein, a spherical end 3 is arranged obliquely above the femoral stem 1.

A bolt 4 is provided under the femoral stem 1.

Preferably, both the spherical end 3 and the bolt 4 are detachably mounted on the femoral stem 1.

Wherein the main part of the bolt 4 is in a shape of a flat rod with a predetermined curvature, and the predetermined curvature is suitably matched with the physiological curvature in the femoral medullary cavity.

Wherein the bolt 4 installed on the femoral stem 1 can be installed on the femoral stem 1 again after rotating 180 degrees around its own axis.

Wherein the femoral stem 1 is provided with a lower slot hole 11 for accommodating the bolt 4.

The bolt 4 includes a main body part in a shape of a flat rod and a plug end 41 at the top.

The cross-sectional shapes of the plug end 41 and the lower slot hole 11 are both centrally symmetrical.

Preferably, the cross-sectional shapes of both the plug end 41 and the lower slot hole 11 are rectangular or waist-shaped.

The beneficial effects of the present invention include the following:

(1) The femoral stem in the bionic artificial hip joint provided by the present invention can be inserted into the corpus femoris along the physiological curvature of the femoral medullary cavity, so as to be in close contact with the corpus femoris, and the stability of the connection between the bionic joint and the corpus femoris and the strength of the femoral shaft are improved by destroying the corpus femoris as little as possible;

(2) The design of the plug connection in the bionic artificial hip joint provided by the present invention can correspond to the physiological curvature of the femoral medullary cavity on the two femurs by changing the angle of installation, that is, a femoral stem with a physiological curvature can be correspondingly installed in any femoral medullary cavity, without the need to prepare two sets of different femoral stems;

(3) According to the bionic artificial hip joint provided by the present invention, a force-bearing part capable of abutting against the inner side of the cortex on greater trochanter is provided on a side of the femoral stem, thereby increasing the longitudinal load of the femoral stem; filling the force-bearing part with cancellous bone, bone strips or stem cells will facilitate the integral growth of the femoral stem and the greater trochanter, thus further improving the stability of the femoral stem while providing supporting force for the femoral stem in another direction.

DESCRIPTION OF THE REFERENCE SIGNS

Figure 1:
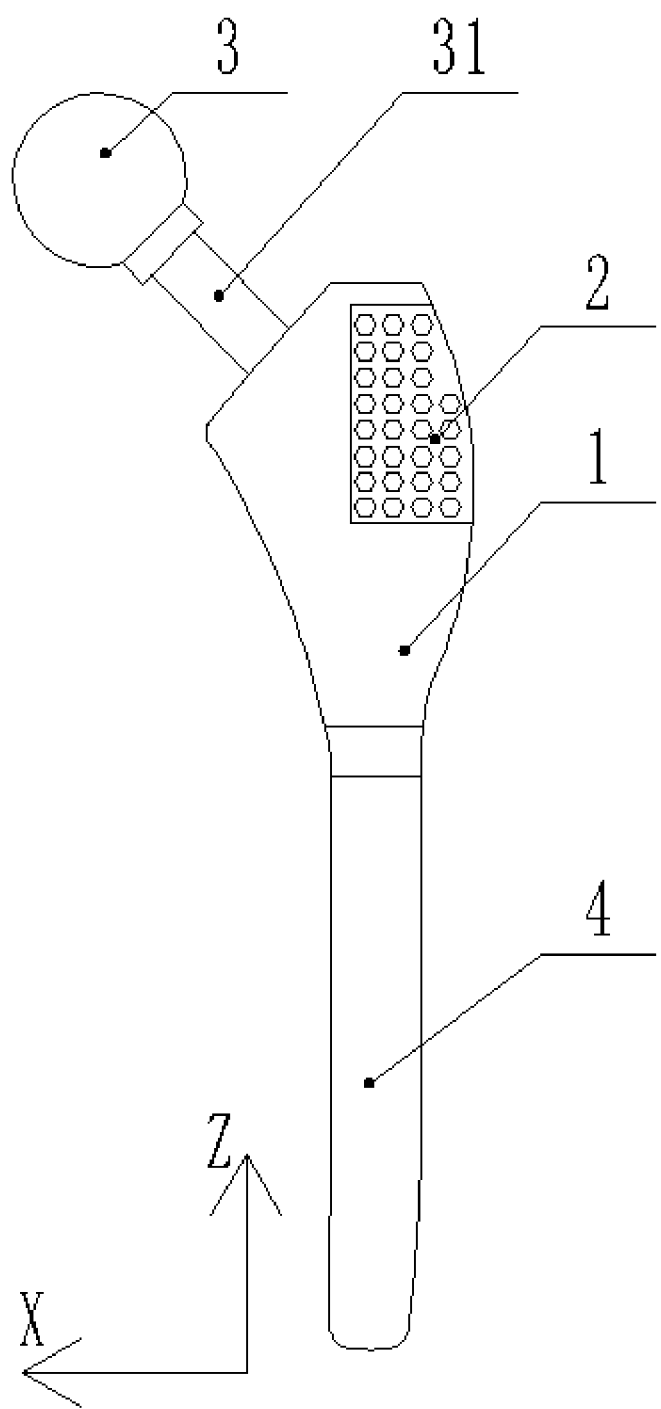
FIG. 1 illustrates a schematic diagram of the overall structure of a bionic artificial hip joint according to a preferred embodiment of the present invention.

1—femoral stem
11—lower slot hole
2—force-bearing part
21—reserved space
22—hole
23—hard shell
24—support ridge
3—spherical end
31—connecting neck
4—bolt
41—plug end

SPECIFIC EMBODIMENTS FOR CARRYING OUT THE INVENTION

The present invention will be further described in detail below through the accompanying drawings and embodiments. Through these descriptions, the characteristics and advantages of the present invention will become clearer.

The word "exemplary" specifically used herein means "serving as an example, embodiment, or illustration." Any embodiment described herein as "exemplary" does not need to be construed as being superior or better than other embodiments. Although various aspects of the embodiments are shown in the drawings, unless otherwise pointed out, the drawings are not necessarily drawn to scale.

Figure 2:
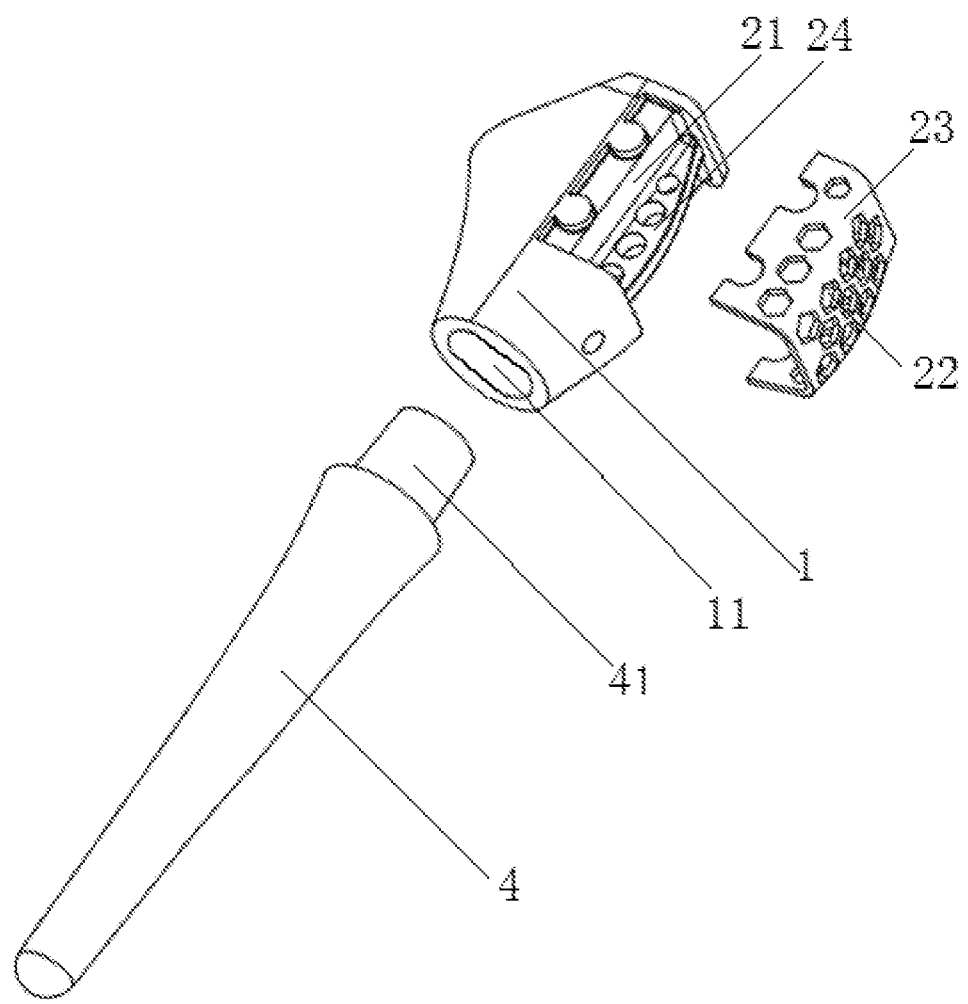
FIG. 2 illustrates an exploded view of a bionic artificial hip joint according to a preferred embodiment of the present invention.

As to the bionic artificial hip joint provided according to the present invention, as shown in FIGS. 1 and 2, the artificial hip joint includes a femoral stem 1 located above corpus femoris. The femoral stem 1 is the core component of the artificial hip joint, the upper part of which is rotatably connected with the hip bone through the spherical end, and the lower part of which is fixedly connected with the femur, so that the artificial hip joint is firmly fixed on the femur and becomes an integrated structure with the femur.

A convex force-bearing part 2 is provided on the femoral stem 1.

The femoral stem 1 can be combined with a cortex on greater trochanter via the force-bearing part 2 to generate an interaction force, i.e., there is an interaction force between the force-bearing part 2 and the cortex on greater trochanter, which can be transmitted to the femoral stem 1, so that force can be transmitted between femoral stem 1 and a cortex on greater trochanter.

The force-bearing part 2 abuts against an inner side of the cortex on greater trochanter.

Preferably, the force-bearing part 2 is located on a side of the femoral stem 1, whose outside is arc-shaped and matches an inner shape of the cortex on greater trochanter. The force-bearing part 2 can be embedded in the arc of the cortex on greater trochanter, thereby improving the contact area between them, making the contact structure between the force-bearing part 2 and the cortex more stable, not easy to shake, and not easy to deflect due to uneven force.

The greater trochanter described in the present invention is a raised area above the outer side of the connected area between the femoral neck and the corpus femoris of the human body. The corpus femoris is the long straight bone in the middle of the femur.

The force-bearing part 2 can be integrated with the cortex on greater trochanter, thereby further improving the degree to which the force-bearing part is combined with the greater trochanter. As such, the consolidation between the bionic artificial hip joint and the femur is further improved.

Figure 3:
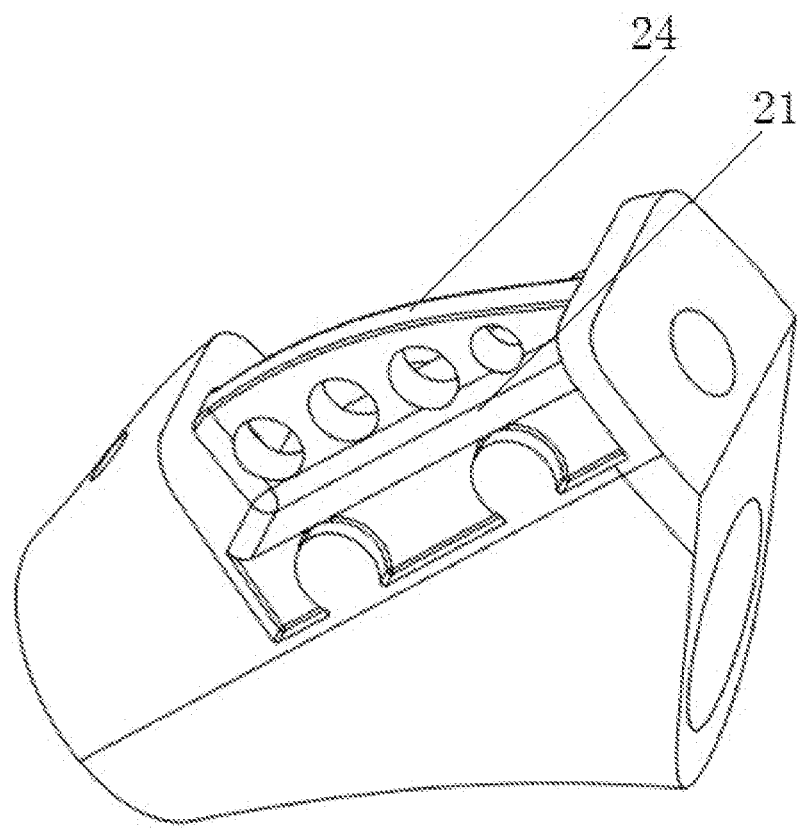
FIG. 3 illustrates a schematic structural diagram of a bionic artificial hip joint according to a preferred embodiment of the present invention with the hard shell removed.

Preferably, as shown in FIGS. 1, 2 and 3, a reserved space 21 capable of containing bone cement is provided inside the force-bearing part 2; a hole 22 communicating with the reserved space 21 is opened via a surface of the force-bearing part 2; the load-bearing part 2 is fixed to the cortex by bone cement, especially bone slag, cancellous bone, and the like can be mixed in the bone cement to facilitate integral growth of the cortex and the force-bearing part 2.

Before installing the bionic artificial hip joint, the reserved space 21 needs to be filled with bone cement, preferably with bone cement mixed with bone slag and cancellous bone.

Preferably, the surface of the force-bearing part 2 is net-shaped, and there are many holes 22 thereon, so as to facilitate integral growth of the bone cement in the reserved space 21 and the cortex, and also to ensure the strength of the load-bearing part, thereby limiting the bone cement and preventing the bone cement from flowing out of the reserved space 21. Preferably, the shape of the hole 22 can be any arbitrary shape, such as a circle, an ellipse, a rectangle, a polygon, etc., which are not particularly limited in the present invention.

Figure 4:
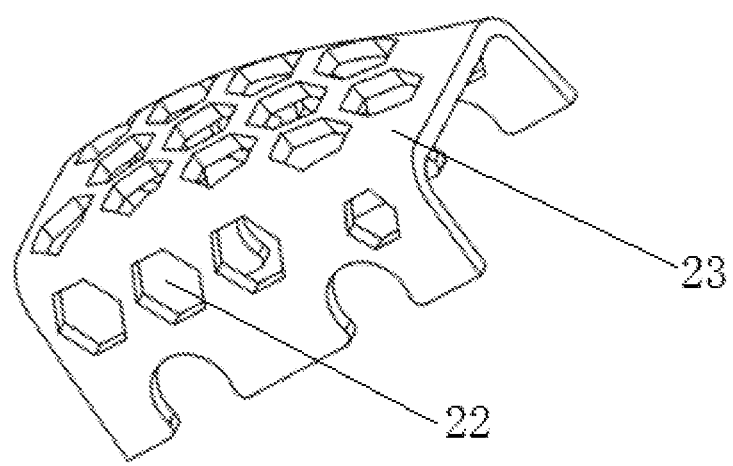
FIG. 4 illustrates a schematic structural diagram of a hard shell in a bionic artificial hip joint according to a preferred embodiment of the present invention.

Further preferably, as shown in FIGS. 3 and 4, the surface of the force-bearing part 2 is a net-shaped hard shell 23, which provides hard protection for the force-bearing part 2 and the bone cement therein.

The hard shell 23 is detachably fixed on the femoral stem 1 to facilitate the injection of bone cement. When bone cement needs to be injected, the hard shell 23 is removed to separate it from the femoral stem 1, so that the reserved space becomes an open space. The hard shell 23 is fastened to the femoral stem 1 after being filled with bone cement, so that the hard shell 23 is in full contact with the bone cement inside, wherein the reserved space 21 is filled with bone cement without voids.

Preferably, the area of the opening on the hard shell 23 should be more than one third, more preferably about a half of the surface area of the hard shell 23.

Preferably, the hard shell 23 and the femoral stem 1 can be detachably connected in a variety of way, e.g., a rotary connection with a rotating shaft, a snap-in connection that achieves a fixing via elasticity of the materials, or a plug structure that uses interference fit for fixing. In the present invention, a snap-in connection is preferred. The hard shell 23 and the femoral stem 1 are provided with a snap-in structure that cooperates with each other. The hard shell 23 has certain elasticity, so that it can be fixed onto the femoral stem 1 and can be detached many times.

In a preferred embodiment, as shown in FIGS. 2 and 3, in the force-bearing part 2, a support ridge 24 is provided on the inner side of the hard shell 23 to support the hard shell 23. There may be one or more support ridges, which are evenly distributed in the reserved space. One end of the support ridge is fixed on the femoral stem 1, i.e., at the bottom of the reserved space, and the other end abuts against the hard shell 23 fitted on the femoral stem 1 to provide support for the hard shell 23 so as to prevent the hard shell 23 from excessively compressing the bone cement when the hard shell 23 is recessed and deformed. Under the action of the support ridge 24, the hard shell 23 is basically not deformed inwardly.

Preferably, a through hole is provided on the wall surface of the support ridge 24, so that the bone cement in the two reserved spaces separated by the support ridge 24 can flow mutually, which also facilitates its subsequent growth with the support ridge 24 into an integral structure.

Since the greater trochanter will generally be removed in the hip joint replacement surgery, fixation by the plug-in relationship between the bolt and the femoral medullary cavity after the artificial hip joint is placed will cause great damage to the human body, and the actual technical effect is not good. By providing the force-bearing part 2, the greater trochanter and the cortex thereon can be retained. The cortex is attached to the force-bearing part 2, and they gradually grow into an integral structure, providing a support point in another direction for the femoral stem. As such, the stability between the femoral stem and the corpus femoris is greatly improved and the life of the artificial hip joint can be extended.

In a preferred embodiment, as shown in FIG. 1, a spherical end 3 is arranged obliquely above the femoral stem 1, and the spherical end 3 is matched with the acetabulum on the hip bone to replace femoral head. Preferably, the spherical end 3 is detachably fixed in the femoral stem 1.

Preferably, the spherical end 3 is provided with a connecting neck 31 which is detachably mounted on the femoral stem 1. Specifically, an upper slot hole is provided on the femoral stem 1. When the spherical end 3 needs to be installed, the connecting neck 31 is inserted into the upper slot hole, and the installation of the spherical end can be completed through interference fit. Preferably, the upper slot hole is a through hole, or a smaller through hole is provided at the bottom of the upper slot hole. As such, air in the upper slot hole can be discharged when the connecting neck 31 is installed, which facilitates the installation of the connecting neck 31.

More preferably, an elastic bumper is provided on the connecting neck 31 to buffer vibration on the bionic joint and prolong the service life.

The elastic bumper includes a compression spring. When an external force acts on the spherical end 3, the spherical end is forced to produce displacement. The elastic bumper is first compressed, and the femoral stem 1 will not be driven to move together until the elastic bumper has been compressed to a certain extent. Moreover, after the external force disappears, the compression spring of the elastic bumper can restore its original state until it is compressed by another external force.

In a preferred embodiment, as shown in FIG. 1, a bolt 4 is provided below the femoral stem 1. The femoral stem 1 and the bolt 4 are detachably fixed. Due to different age and different conditions, the sizes of the femur of patients are different, and it is necessary to select the model and size of the bolt accordingly. For this reason, the femoral stem and the elastic bolt are designed as a detachable non-integrated structure, and the appropriate model and size can be easily selected before use, so as to complete the installation preparations in a fast and convenient way.

The bolt 4 is vertically arranged. The bolt 4 includes a plug end 41 at the top and a main body part below it. The plug end 41 is used to cooperate with the femoral stem 1 and then be fixed on the femoral stem 1. The main body part is used to be inserted into the corpus femoris, or into the femoral medullary cavity of the corpus femoris, and the bionic artificial hip joint is fixed on the corpus femoris through close fit with the femoral medullary cavity.

Figure 5:
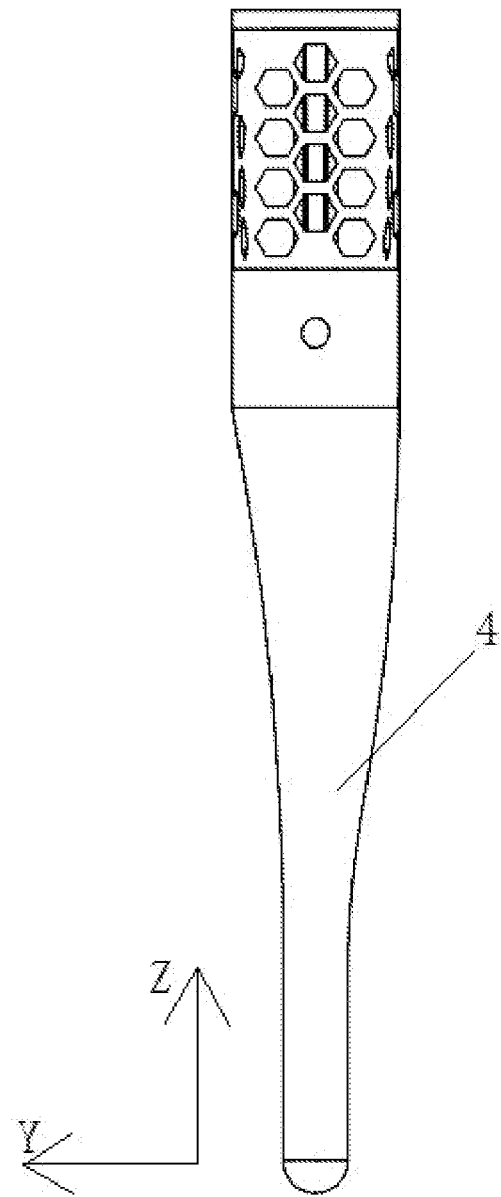
FIG. 5 illustrates a rear view of a bionic artificial hip joint according to a preferred embodiment of the present invention after arranging a bolt with a predetermined curvature.

In a preferred embodiment, the main part of the bolt 4 is in the shape of a flat rod with a predetermined curvature. As shown in FIG. 5, the predetermined curvature is suitably matched with the physiological curvature in the femoral medullary cavity.

The bolt 4 can be inserted into the corpus femoris along the physiological curvature of the femoral medullary cavity on the corpus femoris, thereby fixing the artificial hip joint and the corpus femoris as a whole. Before installing the bolt 4, it is only required to excavate/clear a long hole with a curvature according to the physiological curvature of the femoral medullary cavity, that is, to take out the cancellous bone in the femoral medullary cavity, without using strong destructive means to open the hole or destroying the compact bone substance. As such, it can naturally reduce the damage to the corpus femoris, and will not penetrate the corpus femoris due to operational errors or the thin femoral wall.

Before inserting the bolt 4, only a long hole with a curvature is excavated/cleared in the femoral medullary cavity along its physiological curvature, and the cancellous bone originally in the hole is removed while retaining the compact bone substance. The diameter of the femoral medullary cavity is relatively small, which will be smaller than the outer diameter of the bolt 4. Moreover, the femoral medullary cavity is not a vertical hole, but has a certain curvature. As the bolt 4 gradually deepens, the femoral medullary cavity gradually presses the bolt. When it is inserted to the extreme position, the shape of the bolt fits properly with the curvature of the femoral medullary cavity. The bolt is close to the inner wall of the femoral medullary cavity, that is, it is in full contact with the compact bone substance that constitutes the femoral medullary cavity, and is in close contact with each other. Because the bolt has a predetermined curvature, it is more difficult for the bolt to be detached from the femoral medullary cavity. With natural shock and vibration, it is basically impossible to make the bolt 4 be detached from the femoral medullary cavity.

Preferably, the cross-sectional size of the bolt is gradually changed, and the closer to the lower end, the smaller the cross-sectional size, so as to facilitate the insertion of the bolt into the femoral medullary cavity.

In a preferred embodiment, the bolt has a predetermined curvature, that is, it is bent in one direction. The bending directions in the left and right femurs are opposite. For this reason, the bolt is preferably a symmetrical structure, that is, the bolt 4 on the femur stem 1 can be installed on the femoral stem 1 again after rotating 180 degrees around its own axis. After rotating 180 degrees, the orientation direction of the predetermined curvature of the bolt also naturally changes 180 degrees, facing the opposite direction. For example, the bolt originally applied to the left femur becomes applicable to the right femur after rotating 180 degrees, so that a bolt can be installed on the patient's left or right leg according to actual needs.

Preferably, FIGS. 1 and 5 illustrate a bionic artificial hip joint suitable for installation on the right leg. The X, Y, and Z directions in the present invention are also shown in FIGS. 1 and 5; wherein, the main part of the bolt can be divided into an upper area close to the plug end and a lower area containing the bottom end of the bolt.

In the upper area, the bolt is bent towards the Y-axis direction, that is, towards the front of the human body. Preferably, the bending angle is small, generally about 7-10 degrees.

In the upper area, the thickness of the bolt gradually decreases from top to bottom, that is, the size value in the Y-axis direction gradually decreases. Preferably, the thickness value gradually changes from 15-17 mm to 6-8 mm;

In the upper area, the width of the bolt is basically unchanged, that is, the size value in the X-axis direction is basically unchanged. Preferably, the width value is basically maintained at 10-12 mm.

In the lower area, the bolt is bent towards the X-axis direction, that is, towards the inner side of the human body. Preferably, the bending angle is relatively small, generally about 5-8 degrees; In the lower region, the thickness of the bolt is basically unchanged, that is, the size value in the Y-axis direction is basically unchanged. Preferably, the thickness value is basically maintained at 6-8 mm.

In the lower area, the width of the bolt gradually decreases from top to bottom, that is, the size value in the X-axis direction gradually decreases. Preferably, the width value gradually changes from 10-12 mm to 8-10 mm;

Preferably, there are only two postures that the bolt can be installed on the femoral stem 1, that is, two postures that are 180 degrees different from each other.

The bolt and the femoral stem 1 can be connected in many ways, e.g., a plug structure fixed by interference fit, a nested structure fixed by a horizontal bolt, and a centering structure fixed by a flange plate.

Preferably, when a centering structure is selected, flange plates are provided at the bottom end of the femoral stem and the top end of the bolt, which match each other. The two flange plates can be fixed together by a screw bolt, and the flange plates can rotate relative to each other and be butt-jointed again after rotating 180 degrees.

Preferably, when the nested structure is selected, through holes can be provided at the bottom end of the femoral stem and the top end of the bolt. After the top end of the bolt and the bottom end of the femoral stem are nested, the two through holes overlap, and the through holes can be used for a horizontal bolt to pass through, thereby fixing the bolt and the femoral stem together through the horizontal bolt. Since the through-hole structure can still overlap with another through-hole structure after rotating 180 degrees, the bolt and the femoral stem can be rotated 180 degrees and then be fixed again.

More preferably, a plug structure is selected in the present invention, as shown in FIG. 2, that is, the femoral stem 1 is provided with a lower slot hole 11 for accommodating the bolt 4. The bolt 4 includes a main body part in a shape of a flat rod and a plug end 41 at the top. The cross-sectional shapes of the plug end 41 and the lower slot hole 11 are both centrally symmetrical, that is, do not change after rotating 180 degrees. Preferably, the cross-sectional shapes of both the plug end 41 and the lower slot hole 11 are rectangular or waist-shaped.

The cross-sectional shape of the plug end 41 and the lower slot hole 11 match, so does the cross-sectional size. The plug end 41 is inserted into the lower slot hole 11 via interference fit, and the two are fixed to each other and not easy to be detached.

Further preferably, after the plug end 41 and the lower slot hole 11 are fixed, the bolt 4 and the femoral stem 1 are smoothly transitioned, and when the plug end 41 is rotated 180 degrees, and then inserted and fixed with the lower slot hole 11, the bolt 4 and the femoral stem 1 are still smoothly transitioned.

The present invention further provides a method for using the bionic artificial hip joint. The method comprises:

first selecting an appropriate bolt and a spherical end, and installing them on a femoral stem 1 to form a bionic artificial hip joint, wherein the direction of the predetermined curvature on the bolt is adjusted according to the direction of the physiological curvature of the femoral medullary cavity to be installed;

then removing the hard shell 23 on the femoral stem 1, filling the reserved space 21 with bone cement containing bone slag and cancellous bone, and then buckling and fixing the hard shell 23 on the femoral stem 1; and finally inserting the bolt into the femoral medullary cavity, and attaching the force-bearing part 2 to the inner side of the cortex on greater trochanter, while matching the spherical end with the acetabulum on the hip bone or the substitute structure of the acetabulum.

EXAMPLES

The bionic artificial hip joint provided in the present invention is shown in FIGS. 1, 2 and 5. The femoral stem is provided with a force-bearing part and a bolt. When the bionic artificial hip joint is surgically installed to the body of a patient in need of an artificial hip joint replacement, the force-bearing part and the cortex on greater trochanter can interact, and the plug with a predetermined curvature is inserted into the femoral medullary cavity along the physiological curvature in the femoral medullary cavity.

The relevant performance of the bionic artificial hip joint during and after the operation is as follows:
surgery time: comparable to traditional surgery, about 45 minutes to 60 minutes;
the degree of damage to the human femur during surgery: significantly less than traditional surgery;
surgery difficulty: comparable to traditional surgery;
postoperative recovery effect: significantly better than traditional surgery;
patient experience: better than traditional surgery
the amount/type of exercise that the patient can perform: better than traditional surgery;
the longest service life of the bionic artificial hip joint: better than traditional surgery;
The bionic artificial hip joint showed no obvious loosening after 10-15 years of use.

Comparative Examples

After selecting the artificial hip joint in the prior art and installing the artificial hip joint into the patient's body through surgery, the relevant performance of the bionic artificial hip joint during and after the operation is as follows:
operation time: basically the same;
the degree of damage to the human femur during the operation: very large, the femoral condyle was removed and the bone marrow cavity was damaged;
degree of difficulty of operation: the same;
postoperative recovery effect: not as good as the present invention;
patient experience: not as good as the present invention;
the amount/type of exercise that the patient can perform: not as good as the present invention;
the longest service life of the artificial hip joint: generally 10-15 years;
The artificial hip joint showed loosening, sinking and cortical fracture after 10-15 years of use.

In the description of the present invention, it should be noted that the terms "upper," "lower," "inner," "outer," "front", "rear," etc. indicate the orientation or positional relationship based on the working state of the present invention. The orientation or positional relationship is only for the convenience of describing the present invention and simplifying the description, rather than indicating or implying that the device or element referred to must have a specific orientation, be constructed and operated in a specific orientation, and therefore cannot be understood as limiting the present invention.

The present invention has been described above by combing the preferred embodiments, which are exemplary and only function for illustrations. On the basis of the present invention, various replacements and improvements can be made for the present invention, and they all fall within the scope of protection of the present invention.

What is claimed is:
1. A bionic artificial hip joint, characterized in that,
the artificial hip joint includes a femoral stem (1) located above corpus femoris; and
a convex force-bearing part (2) provided on the femoral stem (1);
the surface of the force-bearing part (2) is covered by a net-shaped hard shell (23) that is arc-shaped and capable to match an inner shape of a cortex on a greater trochanter;
the hard shell (23) is detachably fixed on the force-bearing part (2);
a support ridge (24), a part of the force-bearing part (2), is provided on the inner side of the hard shell (23) to support the hard shell (23);
wherein the hard shell (23) configured to be integrated with the insider of the cortex of the greater trochanter.
2. The bionic artificial hip joint according to claim 1, characterized in that:
a reserved space (21) capable of containing bone cement is provided inside the force-bearing part (2),
a hole (22) communicating with the reserved space (21) is opened via the hard shell (23).
3. The bionic artificial hip joint according to claim 1, characterized in that:
a spherical end (3) is arranged obliquely above the femoral stem (1);
a bolt (4) is provided under the femoral stem (1);
optionally, both the spherical end (3) and the bolt (4) are detachably mounted on the femoral stem (1).
4. The bionic artificial hip joint according to claim 3, characterized in that:
the main part of the bolt (4) is in a shape of a flat rod with a predetermined curvature, and the predetermined curvature is configured to be matched with a physiological curvature in a femoral medullary cavity.
5. The bionic artificial hip joint according to claim 4, characterized in that:
the bolt (4) is placed on the femoral stem (1); the bolt (4) is capable to rotate 180 degrees around its own axis.
6. The bionic artificial hip joint according to claim 5, characterized in that:
the femoral stem (1) is provided with a lower slot hole (11) for accommodating the bolt (4),
the bolt (4) includes a main body part in a shape of a flat rod and a plug end (41) at the top,
the cross-sectional shapes of the plug end (41) and the lower slot hole (11) are both centrally symmetrical;
optionally, the cross-sectional shapes of both the plug end (41) and the lower slot hole (11) are rectangular or waist-shaped.

* * * * *